US008625870B2

(12) United States Patent
Zamyatin et al.

(10) Patent No.: US 8,625,870 B2
(45) Date of Patent: Jan. 7, 2014

(54) METHOD AND SYSTEM FOR SUPPLEMENTING DETAIL IMAGE IN SUCCESSIVE MULTI-SCALE RECONSTRUCTION

(75) Inventors: Alexander Zamyatin, Hawthorn Woods, IL (US); Mihail Petru Dinu, Mundelein, IL (US); Daxin Shi, Vernon Hills, IL (US)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 0 days.

(21) Appl. No.: 13/276,677

(22) Filed: Oct. 19, 2011

(65) Prior Publication Data

US 2013/0101191 A1    Apr. 25, 2013

(51) Int. Cl.
*G06K 9/00* (2006.01)
*A61B 6/00* (2006.01)

(52) U.S. Cl.
USPC .................................. 382/131; 378/4; 378/21

(58) Field of Classification Search
USPC .......... 382/128–134; 378/4, 21–27, 101, 901; 600/407, 410, 411, 425, 427; 128/920, 128/922
See application file for complete search history.

(56) References Cited

U.S. PATENT DOCUMENTS

| 5,909,476 | A  | * | 6/1999  | Cheng et al. ...................... 378/4   |
| 6,381,349 | B1 | * | 4/2002  | Zeng et al. ..................... 382/128   |
| 6,490,476 | B1 | * | 12/2002 | Townsend et al. ............ 600/427        |
| 6,721,387 | B1 | * | 4/2004  | Naidu et al. ...................... 378/8   |

OTHER PUBLICATIONS

Langan, D., Claus, B., Edic, P., Vaillant, R., De Man, B., Basu, S., Iatrou, M., "An iterative algorithm for soft tissue reconstruction from truncated flat panel projections", Medical Imaging 2006: Physics of Medical Imaging, Proceedings of SPIE vol. 6142, 614224 (2006), pp. 614224-1-614224-9.
Ziegler, A., Nielson, T. and Grass, M., "Iterative reconstruction of a region of interest for transmission tomography", Medical Imaging 2006: Physics of Medical Imaging, Proceedings of SPIE vol. 6142, 614223 (2006), pp. 614223-1-614223-12.
Pal, D., Thibault, J., Hsieh, J., Optimization of the field-of-view in a model-based iterative reconstruction for CT, Nuclear Science Symposium Conference Record (NSS/MIC), 2010 IEEE, Oct. 30, 2010-Nov. 6, 2010, pp. 3422-3424.

* cited by examiner

*Primary Examiner* — Abolfazl Tabatabai
(74) *Attorney, Agent, or Firm* — Yoshida & Associates, LLC

(57) ABSTRACT

The image reconstruction method and system reconstructs a multi-scale image using a set of predetermined nested 3D grids, and a zoomed image is reconstructed without losing details. The multiple steps uses a decreasing grid size to reconstruct an ultimately zoomed image in region of interest without degrading image quality.

12 Claims, 5 Drawing Sheets

METHOD AND SYSTEM FOR SUPPLEMENTING DETAIL IMAGE IN SUCCESSIVE MULTI-SCALE RECONSTRUCTION

FIELD OF THE INVENTION

The current invention is generally related to an image processing and system, and more particularly related to multi-scale reconstruction while the image volume grid size is successively decreased.

BACKGROUND OF THE INVENTION

Region of interest (ROI) is zoomed in reconstruction. As ROI is zoomed in an image, the details of the image experience poor quality. Particularly, the challenge becomes apparent for a zoomed image that has been reconstructed using an iterative reconstruction (IR) technique. In general, a reprojection step in IR requires knowledge of the entire object attenuating the x-ray beam. In contrast, analytic filtered back projection (FBP) generally reconstructs an image within the zoomed ROI without the need of the full field of view (FOV) reconstruction, provided that projection data is not truncated.

To overcome the above described challenge in IR, the following approaches have been suggested. Although one prior art technique removed a part of the projection data that corresponds to the outside of ROI in the image volume, the image quality was degraded due to the lacking features in the exterior areas of ROI. Another prior art technique utilized two volume grids including a coarse grid and a fine grid. Unfortunately, the prior art technique was computationally ineffective, and the coarse grid also limited spatial resolution of the fine grid.

In view of the above and other prior art techniques, a multi-scale reconstruction is still desired using not only an iterative reconstruction technique but also an analytic reconstruction technique.

DETAILED DESCRIPTION OF THE EMBODIMENT(S)

Figure 1:
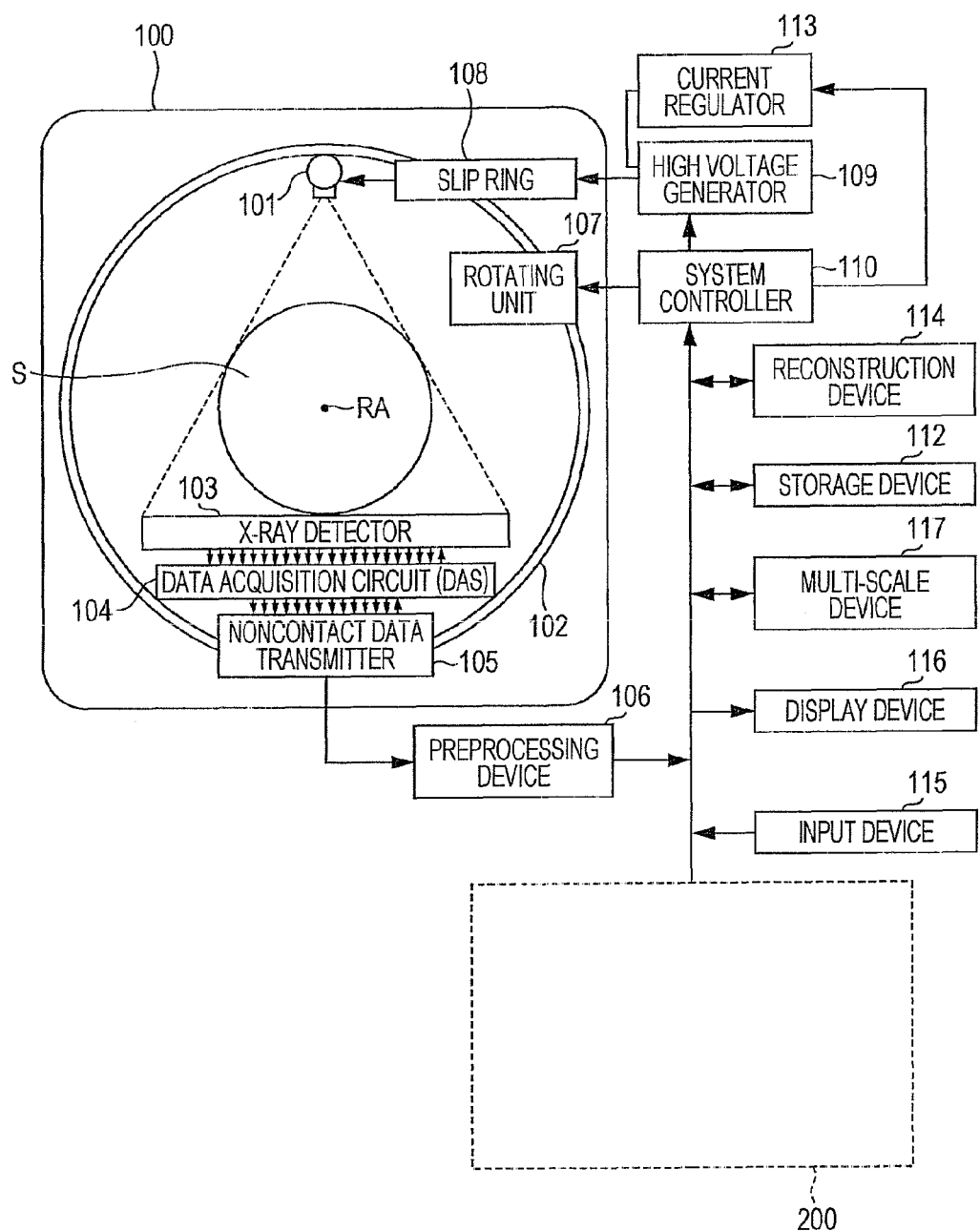
FIG. 1 is a diagram illustrating one embodiment of the multi-slice X-ray CT apparatus or scanner for multi-scale reconstruction according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a side view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that generates a tube voltage to be applied to the X-ray tube 101 through a slip ring 108 so that the X-ray tube 101 generates X ray. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116, multi-scale processing device 117 and the scan plan support apparatus 200. The scan plan support apparatus 200 includes a function for supporting an imaging technician to develop a scan plan.

One embodiment of the reconstruction device 114 further includes various software and hardware components. According to one aspect of the current invention, the reconstruction device 114 of the CT apparatus advantageously minimizes total variation (TV) using an iterative reconstruction technique. In general, the reconstruction device 114 in one embodiment of the current invention operates the total volume iterative reconstruction (TVIR) algorithm, which performs on the projection data simultaneous algebraic reconstruction such an ordered subset simultaneous algebraic reconstruction technique (OS-SART) step and regularization such as a TV minimization step. The two steps are sequentially implemented in the main loop where a number of iterations were prescribed in one embodiment.

Before the TV minimization step, the projection data undergoes an ordered subsets simultaneous algebraic reconstruction technique (OS-SART). The projection data is grouped into a predetermined number of subsets N each having a certain number of views. During the ordered subsets simultaneous algebraic reconstruction technique (OS-SART), each subset may be sequentially processed in one embodiment. In another embodiment, a plurality of the subsets may be processed in parallel by taking advantage of certain microprocessor such as multiple central processing units (CPU) or a graphics processing unit (GPU). In the total variation (TV) minimization step, one embodiment of the reconstruction device 114 employs a line search strategy to search a positive step size so as to ensure the objective function of the current image volume to be smaller than that of the previous image volume.

During the ordered subsets simultaneous algebraic reconstruction technique (OS-SART), the reconstruction device 114 also performs two major operations. Namely, for each subset N, the reconstruction device 114 re-projects the image volume to form the computed projection data and back-projects the normalized difference between the measured projection and the computed projection data to reconstruct an updated image volume. In further detail, one embodiment of the reconstruction device 114 re-projects the image volume by using the ray tracing technique where no coefficient of the system matrix is cached. Moreover, one embodiment of the reconstruction device 114 simultaneously re-projects all rays in a subset, and this is optionally implemented in parallel. In the back-projection, one embodiment of the reconstruction device 114 uses a pixel-driven technique to back-project all of the normalized difference projection data in a subset to form the desired updated image volume. Because the reconstruction device 114 back-projects all ray sums, i.e., difference projection data, in a subset to form an image volume, this operation is optionally implemented in parallel too. These operations are applied to every subset N to complete a single OS-SART step. In addition, AWAD is optionally combined.

In another embodiment of the reconstruction device 114, various other software and hardware components perform a predetermined analytic reconstruction process on the projection data. According to one aspect of the current invention, the reconstruction device 114 of the CT apparatus advantageously reconstructs an image volume by using a predetermined filtered backprojection (FBP) technique. The above described and other embodiments are optionally included in the current scope of the invention as more particularly claimed in the appended claims.

In addition to the above described components, one embodiment of the current invention further includes various other software modules and hardware components for performing multi-scale reconstruction functions. According to one aspect of the current invention, a multi-scale device 117 of the CT apparatus advantageously performs multi-scale reconstruction functions for zooming in on a desired region of interest (ROI) from an original image using a predetermined finer 3D grid. According to another aspect of the invention, one embodiment of the multi-scale device 117 achieves a desired zoom of the ROI through a predetermined number of successive multi-scaling steps where an image is iteratively reconstructed using a decreasing grid size or a decreasing field of view (FOV) size. In other words, the embodiment utilizes a predetermined set of nested 3D grids during the iterative multi-scale reconstruction. As an image is successively zoomed in, details of the image are determined at a successively smaller grid size so that the final zoomed image maintains the desired details.

According to one aspect of the current invention, the multi-scale device 117 accomplishes one exemplary multi-scale reconstruction by determining the output image using only a pair of a coarse grid and a fine grid. In one example, the coarse grid is the original field of view (FOV) while the fine grid is a desired zoom or region of interest (ROI). Using the fine grid size, an image is reconstructed by combining the interpolated image and the detailed image, and the combined output data is outputted as a final desired output image. As necessary, the following iterative process is performed to reconstruct the final desired output image in certain situations.

According to another aspect of the current invention, the multi-scale device 117 accomplishes one exemplary multi-scale reconstruction by iteratively using the output data in combination with a predetermined number of decreasing grid sizes. At each scale of the grid sizes, an image is reconstructed by combining the interpolated image and the detailed image, and the combined output data is used to as a base image for determining a next instance of the interpolated image and the detailed image in the iterative process. A final desired output image is obtained at the end of the above described iterative process when the last scale of the predetermined set of the grid sizes is used. In a strict sense, the iteration begins after the following initial reconstruction using the course and fine grids from an original image.

In one embodiment according to the current invention, the multi-scale device 117 is operationally connected to other software modules and or system components such as the storage device 112, the reconstruction device 114, the display device 116 and the input device 115 via a data/control bus. In this regard, the multi-scale device 117 alone does not necessarily perform multi-scaling functions and or their associated tasks in other embodiments according to the current invention. Furthermore, the multi-scale device 117 is optionally a part of other devices such as the reconstruction device 114 in alternative embodiments according to the current invention.

Figure 2:
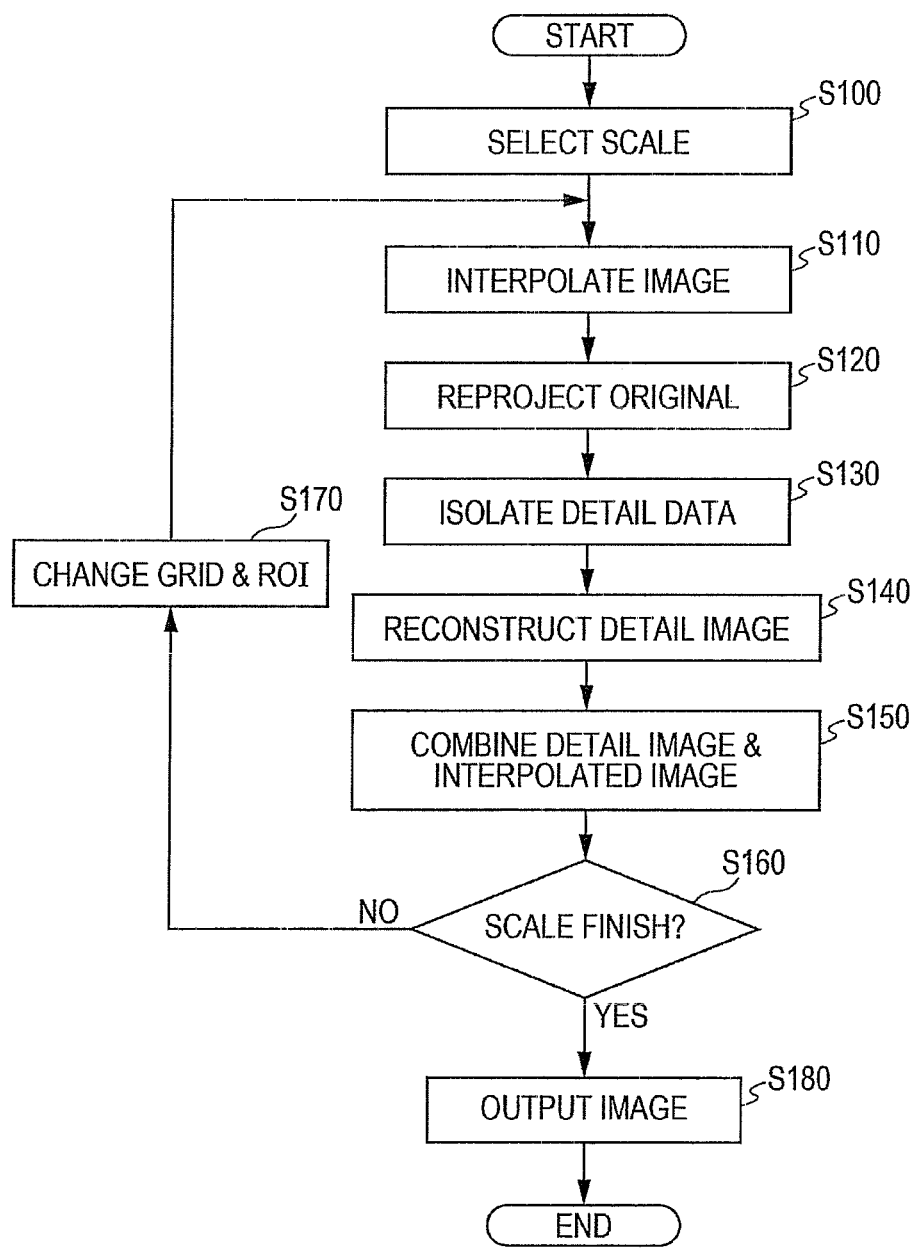
FIG. 2 is a flow chart illustrating steps involved in the multi-scale reconstruction process in one embodiment according to the current invention.

Now referring to FIG. 2, a flow chart illustrates steps involved in the multi-scale reconstruction process in one embodiment according to the current invention. In certain situations, a portion of the reconstructed image is optionally zoomed to a predetermined size. The desired portion is generally a region of interest (ROI). To accomplish the above described zooming of the image, a scale is initially selected in a step S100 based upon the size of the ROI and the desired zoomed image size. One exemplary scale is determined based upon a fine grid size or a fine grid volume in relation to the coarse grid size or the coarse grid volume. In determining the scale, there are other factors that need to be considered in the step S100 for certain kinds of data.

In describing the steps of the multi-scale reconstruction process in one embodiment according to the current invention, the operations are also expressed in equations. For the equations, the above-described scale is expressed in terms of a parameter k=0 and 1, which is used as a subscript for two 3D grids $x_{i,k}$ for the coarse and fine grids. The parameter k determines the pitch size of the grid, and index i indexes all points on the grid. The grid $x_{i,0}$ is the coarse grid having a first pitch size, corresponding to the full field of view while the finer grid $x_{i,1}$ is the fine grid having a second pitch size, corresponding to the desired zoomed field of view. The second pitch size is smaller than the first pitch size in the grids, but the two grids have the same number of pixels. For the two grids at k=0 and 1, the exemplary multi-scale reconstruction process initially reconstructs a full image volume $f_0$ on a coarse grid $x_{i,1}$ from original measure data $r_j^0$ according to a predetermined reconstruction technique RECON1 as expressed in Equation (1)

$$f_0(x_{i,0}) = RECON1[r_j^0] \quad (1)$$

Where the coarse grid size or the coarse grid volume $x_{i,0}$ corresponds to the full or original field of view. According to one exemplary process, the reconstruction technique RECON1 is iterative such as the total volume iterative reconstruction (TVIR) algorithm, which performs on the projection data simultaneous algebraic reconstruction such an ordered subset simultaneous algebraic reconstruction technique (OS-SART) step and regularization such as a TV minimization step. According to another exemplary process, the reconstruction technique RECON1 is optionally a predetermined analytic reconstruction process such as a filtered backprojection (FBP) technique.

Still using an example of the two grids at k=0 and 1, image volume is interpolated in a step S110 on the fine grid volume $x_{i,1}$ from the previously determined full image volume $f_0(x_{i,0})$ to obtain interpolated image volume $\tilde{f}_0(x_{i,1})$. In the following Equation (2.1), a fine grid volume $x_{i,1}$ is obtained at scale k=1.

$$\tilde{f}_0(x_{i,1})=\text{INTPL}\, f_0(x_{i,0}) \tag{2.1}$$

where INTPL is a predetermined interpolation technique such as trilinear interpolation.

In a step S120, the previously reconstructed full image volume $f_0$ is forward projected to obtain a new set of projections $p_j^0$ as shown in Equation (2.2).

$$p_j^0 = \text{FPJ}[f_0] \tag{2.2}$$

FPJ is a predetermined forward projection technique. The reprojected full projection data $p_j^0$ includes some additional information and is different from the original measured data $r_j^0$.

In a step S130, the previously reprojected full projection data $p_j^0$ is subtracted from the original measured data $r_j^0$ to obtain a difference $r_j^1$ as shown in Equation (2.3). In a way, the step S130 isolates some data including some details in a zoomed image.

$$r_j^1 = r_j^0 - p_j^0 \tag{2.3}$$

where the difference $r_j^1$ represents both noise and detail image information in the full image volume. In general, the noise is caused by the difference in the physical pixel size and or by blurring due to the system optics. Furthermore, the more differences are seen within an edge area.

Still using an example of the two predetermined grids at k=0 and 1, the exemplary multi-scale reconstruction process in a step S140 now reconstructs a detail volume $g_1$ on the finer grid $x_{i,1}$ corresponding to the desired zoomed field of view from the previously determined difference $r_j^1$ in Equation (2.3) according to a predetermined reconstruction technique RECON2 as expressed in Equation (2.4).

$$g_1(x_{i,1}) = \text{RECON2}[r_j^1] \tag{2.4}$$

Wherein the predetermined reconstruction technique RECON2 is independent of the predetermined reconstruction technique RECON1. According to one exemplary process, the reconstruction technique RECON2 is iterative such as the total volume iterative reconstruction (TVIR) algorithm, which performs on the projection data simultaneous algebraic reconstruction such an ordered subset simultaneous algebraic reconstruction technique (OS-SART) step and regularization such as a TV minimization step. According to another exemplary process, the reconstruction technique RECON2 is optionally a predetermined analytic reconstruction process such as a filtered backprojection (FBP) technique.

In the example of the two predetermined coarse and fine grids, the exemplary multi-scale reconstruction process in a step S150 now combines the above described detail volume $g_1$ on the finer grid $x_{i,1}$ as defined in Equation (2.4) and the interpolated image volume $\tilde{f}_0$ on the fine grid volume $x_{i,1}$ as defined in Equation (2.1) in order to obtain the desired zoomed output image $f_1$ at scale at k=1 as defined in Equation (2.5).

$$f_1(x_{i,1}) = \tilde{f}_k(x_{i,1}) + g_1(x_{i,1}) \tag{2.5}$$

Obviously, the above described steps in relation to Equations (1) through (2.5) are optionally performed in a predetermined sequential manner, at least in a partially parallel manner or a combination of both. In any case, the exemplary process according to the current invention is not necessarily limited to a particular sequence of the steps, particular equations or particular techniques.

Furthermore, the above described exemplary multi-scale reconstruction technique is optionally expanded to include additional steps to improve the image quality in the zoomed image. The detailed image is optionally iterated at each of the different scale before the ultimate output image is generated in another embodiment of the multi-scale reconstruction according to the current invention.

Instead of using a pair of the coarse and fine grids, the optional steps use a set of several nested 3D grids that are different in size and contain a final grid size for the desired zoomed image. For example, if 80 millimeter (mm) field of view (FOV) is to be reconstructed, the multi-scale reconstruction process in one embodiment reconstructs a 320 mm region of interest (ROI) that is followed by a 160 mm ROI before the multi-scale reconstruction process ultimately reconstructs the 80 mm ROI according to the current invention. The ROIs are all centered in the same position. Accordingly, the scale is expressed in terms of a parameter k, which is used as a subscript for a set of several nested 3D grids $x_{i,k}$. The parameter k determines the pitch size of the grid, and index i indexes all points on the grid. The grid $x_{i,0}$ is the coarsest grid, corresponding to the full field of view. As k increases, grids become finer.

In optional steps of the multi-scale reconstruction process in one embodiment according to the current invention, the output image is iteratively processed to obtain a final zoomed image in multi-scale reconstruction steps. Using the above example of obtaining the 80 mm FOV from reconstructing the 320 ROI in a predetermined sequential manner, the scale k ranges from 0 to 2 for the nested 3D grids $x_{i,k}$.

With respect to the flow chart as illustrated to FIG. 2, a step S160 determines whether or not the additional steps are to be performed using a different scale. If it is determined that no step at a additional scale is to be performed, the multi-scale reconstruction process in one embodiment according to the current invention outputs in a step S180 the desired zoomed output image $f_1$ at scale at k=1 as defined in Equation (2.5). On the other hand, the step S160 determines that further steps at a additional scale are to be performed, the multi-scale reconstruction process according to the current invention proceeds to a step S170, where the grid with a next smaller pitch size is selected by incrementing a value of the parameter k by one and proceeds to the step S110. At the same time in the step S170, a smaller one of the predetermined ROIs is also selected to zoom in. This is a start of iterative process to generate a next instance of the multi-scale reconstruction process according to the current invention.

At scale k=2, the above described values of given $g_k(x_{i,k})$ and $f_k(x_{i,k})$ at k=1 are used during the initial iteration instance. Subsequently, the values of a previous instance are used in a next instance during the iteration until a predetermined number of the iterative process is completed. In the next instance of the step S110 at k=2, image volume is interpolated in a step S110 on a next fine grid volume $x_{i,k+1}$ from the previously determined full image volume $f_k(x_{i,k})$ to obtain interpolated image volume $\tilde{f}_k(x_{i,k+1})$. In the following Equation (3.1), a fine grid volume $x_{i,k+1}$ is obtained at scale k=2.

$$\tilde{f}_k(x_{i,k+1}) = \text{INTPL}\, f_k(x_{i,k}) \tag{3.1}$$

where INTPL is a predetermined interpolation technique such as trilinear interpolation.

In a next instance of the step S120, the previously reconstructed detailed image volume $g_k$ is forward projected to obtain a new set of projections $p_j^k$ for detailed image volume as shown in Equation (3.2).

$$p_j^k = \text{FPJ}[g_k] \quad (3.2)$$

FPJ is a predetermined forward projection technique. The reprojected projection data $p_j^k$ includes some additional information and is different from the previously determined difference $r_j^k$.

In a next instance of the step S130, the previously reprojected full projection data $p_j^k$ is subtracted from the previously determined difference $r_j^k$ to obtain a difference $r_j^{k+1}$ as shown in Equation (3.3). In a way, the step S130 isolates some data including some details in a zoomed image.

$$r_j^{k+1} = r_j^k - p_j^k \quad (3.3)$$

where the difference $r_j^{k+1}$ represents both noise and detail image information in the detailed image volume. In general, the noise is caused by the difference in the physical pixel size and or by blurring due to the system optics. Furthermore, the more differences are seen within an edge area.

Still using an example of the two predetermined grids at k=k+1, the exemplary multi-scale reconstruction process in a next instance of the step S140 now reconstructs a detail volume $g_{k+1}$ on the finer grid $x_{i,k+1}$ corresponding to the zoomed field of view from the previously determined difference $r_j^{k+1}$ in Equation (3.3) according to a predetermined reconstruction technique RECON2 as expressed in Equation (3.4).

$$g_{k+1}(x_{i,k+1}) = \text{RECON2}[r_j^{k+1}] \quad (3.4)$$

Wherein the predetermined reconstruction technique RECON2 is independent of the predetermined reconstruction technique RECON1. According to one exemplary process, the reconstruction technique RECON2 is iterative such as the total volume iterative reconstruction (TVIR) algorithm, which performs on the projection data simultaneous algebraic reconstruction such an ordered subset simultaneous algebraic reconstruction technique (OS-SART) step and regularization such as a TV minimization step. According to another exemplary process, the reconstruction technique RECON2 is optionally a predetermined analytic reconstruction process such as a filtered backprojection (FBP) technique.

In the example of the optional multiple fine grids, the exemplary multi-scale reconstruction process in a next instance of the step S150 now combines the above described detail volume $g_{k+1}$ on the finer grid $x_{i,k+1}$ as defined in Equation (3.4) and the interpolated image volume $\tilde{f}_k$ on the fine grid volume $x_{i,k+1}$ as defined in Equation (3.1) in order to obtain the desired zoomed output image $f_k$ at scale at k=k+1 as defined in Equation (3.5).

$$f_{k+1}(x_{i,k+1}) = \tilde{f}_k(x_{i,k+1}) + g_{k+1}(x_{i,k+1}) \quad (3.5)$$

Obviously, the above described steps are optionally performed in a predetermined sequential manner, at least in a partially parallel manner or a combination of both. In any case, the exemplary process according to the current invention is not limited to a particular sequence of the steps, particular equations or particular techniques even during the iteration in order to practice the current invention.

A next instance of the step S160 again determines whether or not the additional steps are to be performed using a different scale. If it is determined that no step at a additional scale is to be performed, the multi-scale reconstruction process in one embodiment according to the current invention outputs in the step S180 the desired zoomed output image $f_{k+1}$ at scale at k=k+1 as defined in Equation (3.5). On the other hand, the step S160 determines that further steps at a additional scale are to be performed, the multi-scale reconstruction process according to the current invention proceeds to the step S170, where the grid in a next size is selected by incrementing a value of the parameter k by one and proceeds to the step S110. This is a start of the next instance of the iterative process to generate an additional instance of the multi-scale reconstruction process according to the current invention.

Figure 3A:
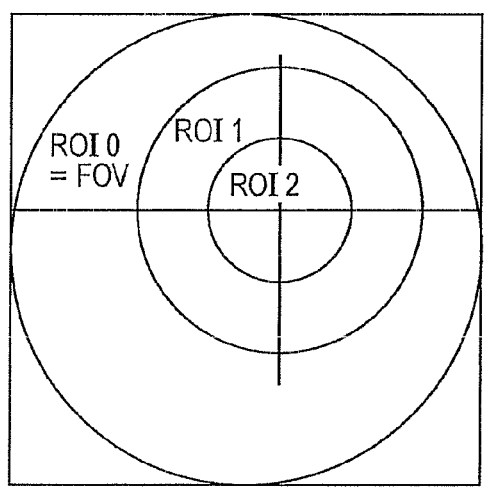
FIG. 3 is a diagram illustrating a set of ROIs and a corresponding set of nested 3D grids that are different in size and contain a final grid size for the desired zoomed image according to the current inventions.
Figure 3B:
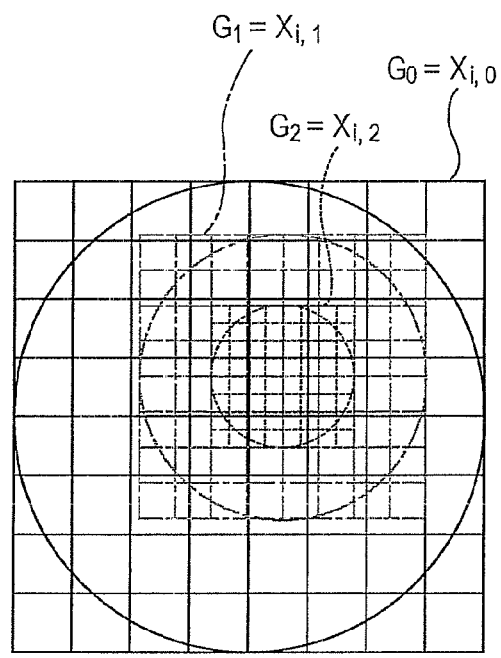

Now referring to FIG. 3, a diagram illustrates a set of predetermined nested ROIs and corresponding 3D grids that are different in size and contain a final grid size for the desired zoomed image. FIG. 3A illustrates a predetermined set of three ROIs including ROI 0, which is field of view (FOV), a smaller region of interest ROI 1 and a final desired or the smallest region of interest ROI 2. FIG. 3B illustrates a predetermined set of three nested grids including $G_0$, which is an original grid, a smaller grid $G_1$ and the smallest grid $G_2$. Size each of these grids $G_0$, $G_1$ and $G_2$ has the same number of pixels, the grid size remains constant during the multi-scale reconstruction process. For example, the grid size is 512×512. Thus, the grid spacing or pitch becomes smaller during the multi-scale reconstruction process as the grid index increases from $G_0$ to $G_1$ and from $G_1$ to $G_2$. In general, the grid spacing or pitch is defined to be "ROI size/Grid size."

For example, if the final ROI 2 of 40 millimeter (mm) field of view (FOV) is to be reconstructed, the multi-scale reconstruction process in one embodiment reconstructs using an original grid $G_0$ to generate a 160 mm region of interest (ROI). Then, the multi-scale reconstruction process uses a second grid $G_1$ to generate a 80 mm ROI 1 before the multi-scale reconstruction process uses a third grid $G_3$ to reconstruct the 40 mm ROI. The ROIs and the grids are all centered in the same position. Accordingly, the scale is expressed in terms of a parameter k, which is used as a subscript for a set of several nested 3D grids. The parameter k determines the pitch size of the grid, and index i indexes all points on the grid. In the above example, the grid is reduced in size by one half in generating a set of the grids. The current invention is not limited to any particular reduction scheme.

Figure 4A:
FIGS. 4A and 4B illustrate the effects of the multi-scale reconstruction in one example comparison according to the current invention.
Figure 4B:

Now referring to FIGS. 4A and 4B, the effects of the multi-scale reconstruction are illustrated in one example comparison according to the current invention. FIG. 4A illustrates a lung image that has been zoomed in using a prior art technique. FIG. 4B illustrates the same lung image that has been zoomed in using the multi-scale iteration reconstruction technique according to the current invention. The multi-scale iteration reconstruction technique utilized the OS-SART over 20 iterations and a two-step multi-scale reconstruction from 500 mm to 320 mm.

Figure 5:
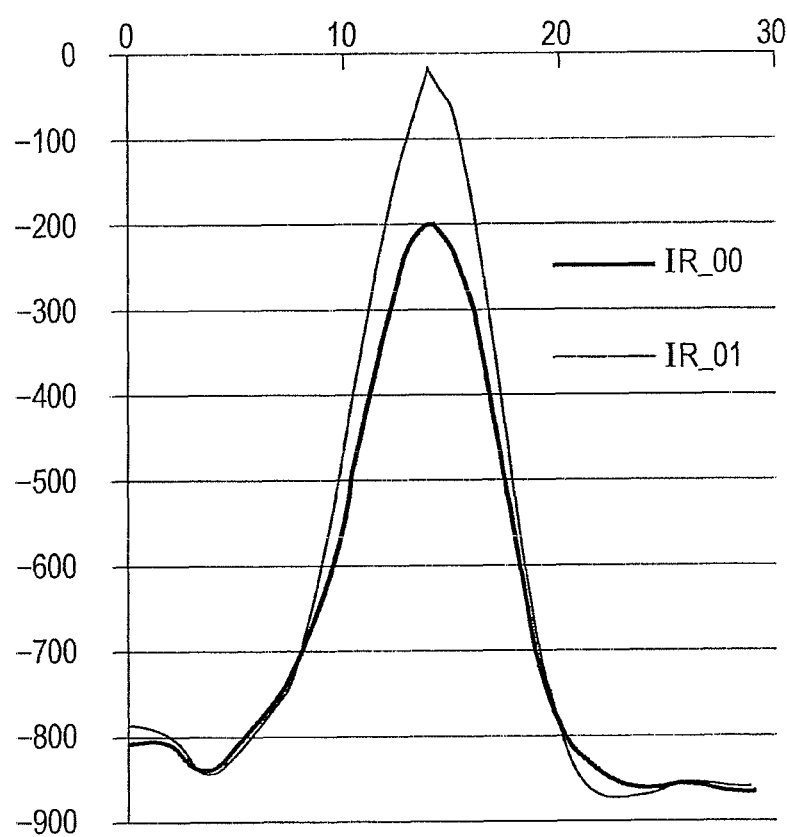
FIG. 5 is a graph illustrating a line profile as measured across the lung vessel.

Now referring to FIG. 5, a graph illustrating a line profile as measured across the lung vessel. The x-axis is the image pixel coordinate while the y-axis is the corresponding HU value. Furthermore, IOLD signifies two-grid approach (IR_00) or old IR of prior art. On the other hand, INEW signifies the 2-step approach (IR_01) or new IR of the multi-scale iterative reconstruction technique according to the current invention. The line profile is measured across the lung vessel, and the graph shows that the multi-scale iterative reconstruction technique according to the current invention enhances vessel visibility.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of multi-scale reconstruction in computed tomography, comprising the steps of:
   a) reconstructing a full image based upon original data;
   b) interpolating a first predetermined region of interest (ROI) from the full image to obtain a first interpolated image;
   c) reprojecting the full image to first reprojected data;
   d) subtracting the first reprojected data from the original data to obtain first difference data, the first difference data representing noise and detail image components;
   e) reconstructing a first detail image using the first difference data; and
   f) obtaining a first output image by combining the first detail image and the first interpolated image.

2. The method of multi-scale reconstruction in computed tomography according to claim 1 further comprising the additional steps of:
   g) further interpolating a second predetermined region of interest (ROI) from the first output image to obtain a second interpolated image, the second predetermined ROI being smaller than the first predetermined ROI;
   h) reprojecting the first detailed image to obtain second reprojected data;
   i) subtracting the second reprojected data from the first difference data to obtain second difference data, the second difference data representing noise and refined detail image components;
   j) reconstructing a portion of the second difference to obtain a second detail image; and
   k) obtaining a second output image by combining the second detail image and the second interpolated image.

3. The method of multi-scale reconstruction in computed tomography according to claim 2 wherein the steps g) through k) are iteratively repeated for a predetermined number of iterations based upon a current instance of the steps g) through k) to obtain a next instance of the second output image as the second predetermined ROI decreases over each of the iterations.

4. The method of multi-scale reconstruction in computed tomography according to claim 3 wherein the predetermined second ROI decreases in size by a predetermined fraction over each of the iterations.

5. The method of multi-scale reconstruction in computed tomography according to claim 2 wherein step j) is reconstructed using either an analytical reconstruction technique or an iterative reconstruction technique.

6. The method of multi-scale reconstruction in computed tomography according to claim 1 wherein the steps a) and e) are reconstructed using a combination of an analytical reconstruction technique and an iterative reconstruction technique.

7. A system for multi-scale reconstruction in computed tomography, comprising:
   a reconstruction device for reconstructing a full image based upon original data; and
   a multi-scale device connected to said reconstruction device for interpolating a first predetermined region of interest (ROI) from the full image to obtain a first interpolated image, said multi-scale device reprojecting the full image to first reprojected data, said multi-scale device subtracting the first reprojected data from the original data to obtain first difference data, the first difference data representing noise and detail image components, wherein said reconstruction device reconstructs a first detail image using the first difference data, said multi-scale device obtains a first output image by combining the first detail image and the first interpolated image.

8. The system for multi-scale reconstruction in computed tomography according to claim 7 wherein said multi-scale device further interpolates the second predetermined region of interest (ROI) from the first output image to obtain a second interpolated image, the second predetermined ROI being smaller than the first predetermined ROI, said multi-scale device reprojecting the first detailed image to obtain second reprojected data, said multi-scale device subtracting the second reprojected data from the first difference data to obtain second difference data, the second difference data representing noise and refined detail image components, wherein said reconstruction device reconstructs a second detail image using the second difference data, said multi-scale device obtains a second output image by combining the second detail image and the second interpolated image.

9. The system for multi-scale reconstruction in computed tomography according to claim 8 wherein said multi-scale device iteratively repeats for a predetermined number of iterations based upon a current instance of the second output image and the second detail image to obtain a next instance of the second output image as the predetermined second ROI decreases over each of the iterations.

10. The system for multi-scale reconstruction in computed tomography according to claim 9 wherein the second predetermined ROI decreases in size by a predetermined fraction over each of the iterations.

11. The system for multi-scale reconstruction in computed tomography according to claim 8 wherein said reconstruction device reconstructs the image using either an analytical reconstruction technique or an iterative reconstruction technique.

12. The system for multi-scale reconstruction in computed tomography according to claim 7 wherein said reconstruction device reconstructs the image using a combination of an analytical reconstruction technique and an iterative reconstruction technique.

* * * * *